United States Patent [19]
Fitch

[11] Patent Number: 5,919,128
[45] Date of Patent: Jul. 6, 1999

[54] SPARSE APERTURE ENDOSCOPE

[75] Inventor: Joseph P. Fitch, Livermore, Calif.

[73] Assignee: The Regents of the University of California, Oakland, Calif.

[21] Appl. No.: 08/877,714

[22] Filed: Jun. 18, 1997

[51] Int. Cl.⁶ .................................................. A61B 1/06
[52] U.S. Cl. ........................ 600/166; 600/111; 600/176
[58] Field of Search .................................. 600/111, 113, 600/129, 130, 166, 173, 176, 143, 182; 359/462; 348/65, 75

[56] References Cited

U.S. PATENT DOCUMENTS

| | | | |
|---|---|---|---|
| 4,217,891 | 8/1980 | Carson | 600/182 |
| 4,919,114 | 4/1990 | Miyazaki | 600/173 |
| 4,924,853 | 5/1990 | Jones et al. | 600/166 |
| 5,166,787 | 11/1992 | Irion | 348/75 |
| 5,305,121 | 4/1994 | Moll | 348/65 |
| 5,437,626 | 8/1995 | Cohen et al. | 600/182 |
| 5,603,687 | 2/1997 | Hori et al. | 600/111 |
| 5,743,847 | 4/1998 | Nakamura et al. | 600/111 |

FOREIGN PATENT DOCUMENTS

| 305170 | 3/1989 | European Pat. Off. | 600/182 |
|---|---|---|---|

*Primary Examiner*—John P. Leubecker
*Assistant Examiner*—Ira Hatton
*Attorney, Agent, or Firm*—L. E. Carnahan

[57] ABSTRACT

An endoscope which reduces the volume needed by the imaging part thereof, maintains resolution of a wide diameter optical system, while increasing tool access, and allows stereographic or interferometric processing for depth and perspective information/visualization. Because the endoscope decreases the volume consumed by imaging optics such allows a larger fraction of the volume to be used for non-imaging tools, which allows smaller incisions in surgical and diagnostic medical applications thus produces less trauma to the patient or allows access to smaller volumes than is possible with larger instruments. The endoscope utilizes fiber optic light pipes in an outer layer for illumination, a multi-pupil imaging system in an inner annulus, and an access channel for other tools in the center. The endoscope is amenable to implementation as a flexible scope, and thus increases the utility thereof. Because the endoscope uses a multi-aperture pupil, it can also be utilized as an optical array, allowing stereographic and interferometric processing.

25 Claims, 2 Drawing Sheets

SPARSE APERTURE ENDOSCOPE

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to endoscopes, particularly to an endoscope utilizing fiber optic light pipes for illumination, and more particularly to an endoscope which additionally utilizes a multi-pupil imaging system and a central access channel for tools.

Endoscopes are widely used in medicine and other applications, such as inspecting internal and difficult to see/access components of mechanical systems. Existing endoscopes are one of three types: 1) fixed optic telescopes where image is relayed optically (monocular or binocular to produce stereo depth perception; 2) flexible or semi-rigid fiber optic bundles (each fiber is a pixel); and 3) end-mounted camera (CCD) systems where the digital detector is placed in the tip with the imaging optics. There has been a need for improving tools used in laproscopic and other videoscopic medical procedures. The endoscope of this invention satisfies this prior need by: 1) reducing the volume needed by the imaging part of an endoscope; 2) maintains resolution of a wide diameter optical system, but increases tool access; and 3) allows stereographic or interferometric processing for depth and perspective information/visualization. In place of the single pupil imaging lens of a typical prior known endoscope, the endoscope of this invention utilizes a multi-pupil imaging system within which is an access channel for tools.

SUMMARY OF THE INVENTION

It is an object of the present invention to provide an improved endoscope.

A further object of the invention is to provide an endoscope with decreased volume of the imaging optics.

A further object of the invention is to provide an endoscope which allows for smaller incisions or openings through which it can be inserted.

Another object of the invention is to provide an endoscope having an access channel for tools, etc.

Another object of the invention is to provide an endoscope which can be increased in diameter at its point of use.

Another object of the invention is to provide an endoscope with a multi-pupil imaging system.

Another object of the invention is to provide an endoscope which reduces the volume needed for imaging, maintains resolution of a wide diameter optical system, increases tool access, and allows for stereographic or interferometric processing for depth and perspective information/visualization.

Another object of the invention is to provide an endoscope which in addition to the use of fiber optic light pipes for illumination, utilizes a multi-pupil imaging system, and a centrally located access channel for tools, etc.

Other objects and advantages of the present invention will become apparent from the following description and accompanying drawings. The invention is directed to an endoscope which utilizes a multi-pupil imaging system and an access channel for tools, etc., as well as fiber optic light pipes for illumination. The endoscope of the present invention decreases the volume normally consumed by the imaging optics allowing a larger fraction of the volume to be used for non-imaging tools. In surgery and diagnostic medicine, this allows smaller incisions which produce less trauma to the patient or allows access to smaller volumes than is possible with larger instruments. The medical advantages are reduced pain and decreased time for healing. The endoscope of this invention is also amenable to implementation as a flexible scope, thus increasing the utility. Also, because the endoscope uses a multi-aperture pupil, it can be treated as an optical array, allowing stereographic and interferometric processing for depth and perspective information. The endoscope of this invention has particular application as a tool in minimally invasive medicine, with potential application in general surgery as well as catheter-based procedures in the treatment of vascular diseases like stroke and stroke causing conditions. The endoscope has non-medical applications such as inspecting internal and difficult to see/access components of mechanical systems, such as seeing behind engine parts.

BRIEF DESCRIPTION OF THE DRAWINGS

The accompanying drawings, which are incorporated into and form a part of the disclosure, illustrate embodiments of the invention and, together with the description, serve to explain the principles of the invention.

DETAILED DESCRIPTION OF THE INVENTION

The present invention is directed to a sparse aperture endoscope. Endoscopes are widely used in medicine and other applications for internal inspection purposes, and are particularly useful in laproscopic and other videoscopic medical procedures. The invention: 1) reduces the volume needed by the imaging part of the endoscope; 2) maintains resolution of a wide diameter optical system, but increases tool access; and 3) allows stereographic or interferometric processing for depth and perspective information/visualization.

Existing endoscopes designs fall into one of three types:
1. Fixed optic telescopes where image is relayed optically (monocular or binocular to produce stereo depth perception).
2. Flexible or semi-rigid fiber optic bundles (each fiber a pixel).
3. End-mounted camera (CCD) systems where the digital detector is placed in the tip with the imaging optics.

The endoscope of the present invention impacts the types of designs 1 and 2 above, and the size and weight constrains of all three prior designs. The present invention affects both size and weight because of a hollow core (or multiple channels) which can be produced with no reduction in image quality (spatial resolution).

Figure 1:
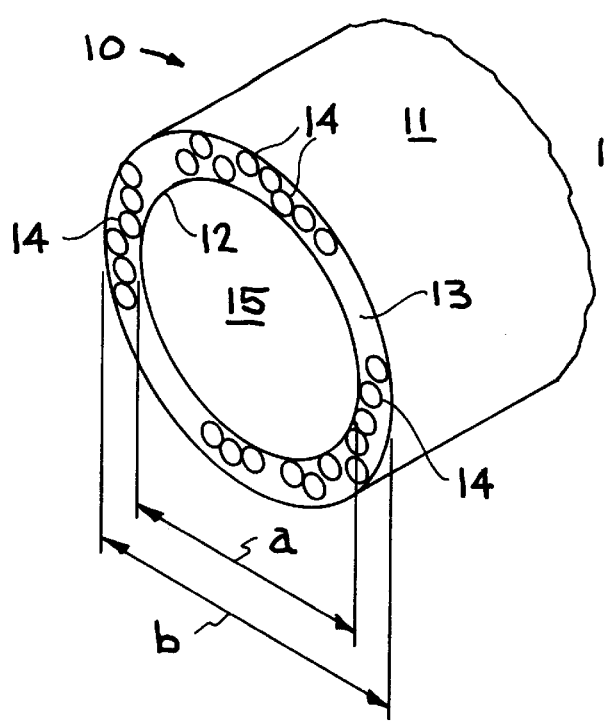
FIG. 1 illustrates an end section of a typical prior art endoscope.

FIG. 1 illustrates a typical prior art endoscope indicated at 10 and composed of an outer tube or member 11 and an inner tube or member 12 between which is a space or annulus 13 within which are positioned a plurality of fiber optic light pipes 14 for illumination, and with a single pupil imaging lens 15 in the inner member 12. In this typical prior art endoscope, the video is collected through the center lens 15 using relay optics down the length of the endoscope (sometimes over 30 cm) and the fiber optics 14 are connected to a light source for illumination only. The inner diameter, a, of inner member 12 is also the diameter of lens 15 (which determines the spatial resolution of the system). The outer diameter, b, of the outer member 11 determines the overall size of the endoscope 10.

Figure 2:
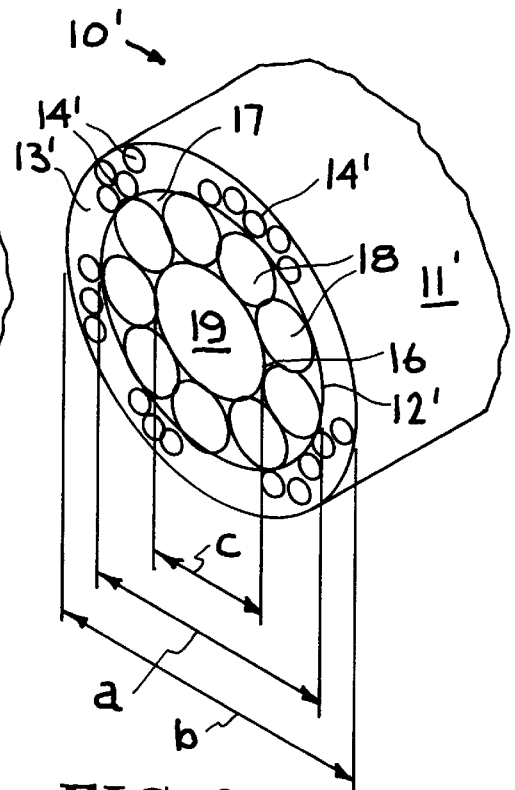
FIG. 2 illustrates an end section of an embodiment of an endoscope made in accordance with the present invention.

FIG. 2 illustrates an embodiment of an endoscope made in accordance with the present invention, and components which correspond to the FIG. 1 prior art endoscope will be given corresponding reference numerals. The basic difference be the FIG. 2 and FIG. 1 endoscopes is that FIG. 2 utilizes a multi-pupil imaging system and has a central access channel for tools, etc. As shown in FIG. 2, the endoscope of this invention, generally indicated at 10', utilizes, like the FIG. 1 endoscope, an outer tube or member 11', and inner tube or member 12', between which is a space or annulus 13' in which are positioned a plurality of fiber optic light pipes 14' for illumination purposes. In FIG. 2, central tube or member 16 to be positioned within inner member 12' and between which is defined a space or annulus 17 in which is located a plurality of pupil imaging lens 18 forming a multi-pupil imaging system. The interior of central tube or member defines a hollow access channel 19, through which tools, etc. may be passed. In the FIG. 2 embodiment, the video is collected through the multi-pupil array 18 using relay optics down the length of the endoscope or via fiber optic bundles. As in the FIG. 1 endoscope the fiber optics 14' in the annulus 13' are connected to a light source for illumination only. In FIG. 2, the diameter, a, is the effective lens diameter (which determines the spatial resolution of the system and can be achieved with many different multi-pupil patterns). The outer diameter, b, determines the overall size of the instrument. The inner diameter, c, determines the size of the largest tool or instrument, etc., that can be manipulated through the endoscope via access channel 19. The multiple pupils or lens 18 must be "combined" to form an image, just as in multi-aperture telescopes used in astronomy.

Figure 3:
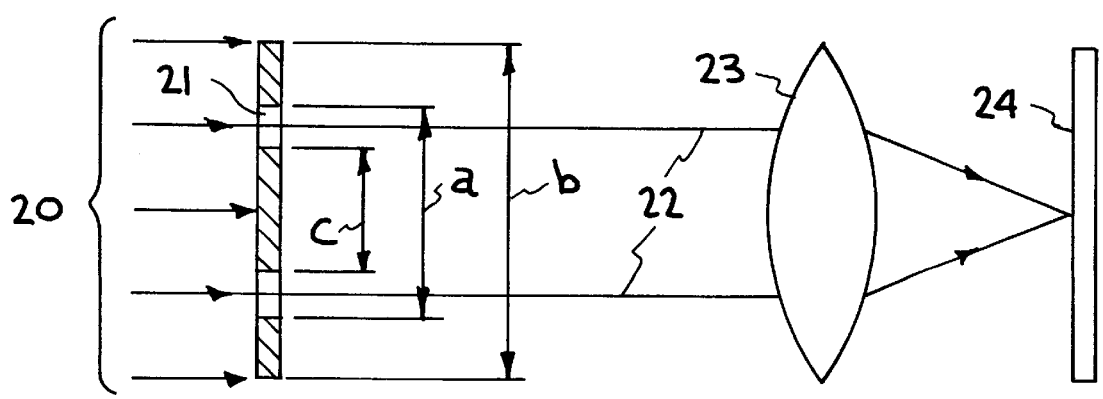
FIG. 3 is a schematic illustration of an optical system utilizing an embodiment of an endoscope of the present invention.

FIG. 3 schematically illustrates an optical system using the multi-pupil imaging system of FIG. 2. In the optical system of FIG. 3, the optical transfer function for incoherent illumination covers the same spatial frequencies as a single aperture system. As shown, light from the scene of interest indicated by arrows 20 is collected through multiple pupils 21 into an optical relay 22 (optics or fibers) to a combining optics 23 and onto an image plane 24 or for stereographic or interferometric array processing. The dimensions a, b, and c, are as described above with respect to FIG. 2.

By way of example, in the FIG. 2 embodiment, the tube or member 11 may have an outer-diameter (O.D.) "b" of 1 to 20 mm, wall thickness of 0.1 to 1 mm, and be constructed of metal, plastic, rubber, or glass; the tube or member 12' may have an inner diameter (I.D.) "a", of 0.8 to 19.8 mm, wall thickness of 0.05 to 1 mm, and be constructed of metal, plastic, rubber, or glass; the tube or member 16 may have an inner diameter (I.D.) "c" of 0.6 to 19.6 mm, wall thickness of 0.05 to 1 mm, and be constructed of metal, plastic, rubber, or glass; with the lens 18 having a diameter of 0.5 to 10 mm, and constructed of glass or plastic, with either a concave or convex surface or glass or plastic fiber optics filling the lens space. The fiber optic light pipes 14' may have a diameter of 0.01 to 0.5 mm.

Figure 4:
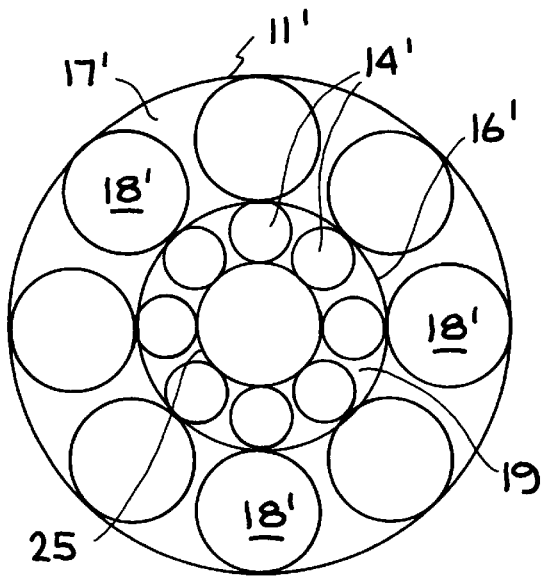
FIGS. 4 and 5 illustrate end sections of other embodiments of the invention.
Figure 5:
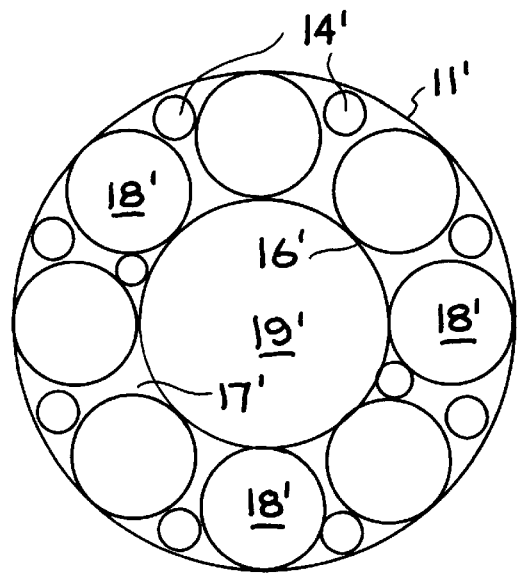

FIGS. 4 and 5 illustrate an embodiment of the invention wherein the fiber optics are not located on the outside of the imaging lens as in FIG. 2. In FIG. 4, the fiber optic light pipes 14' are located within a central tube or member 16' and are mounted around a small center tube 25, with the lens 18' located around tube 16. In the FIG. 5 embodiment the fiber optic light pipes 14' are located in the space or annulus 17' intermediate outer tube 11' and tube 16'; and are interspersed among the lens 18'.

Figure 6A:
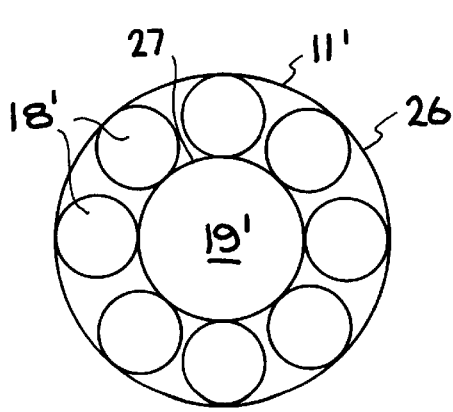
FIGS. 6A and 6B illustrate an embodiment capable of increased spatial resolution after entry in a body cavity.
Figure 6B:
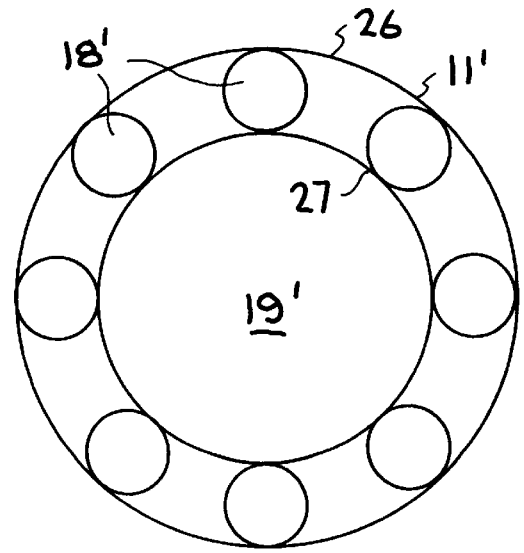

FIGS. 6A and 6B illustrate an embodiment, without the light pipes being shown, wherein the use of multiple lens allows movement thereof so that the outer diameter can be small upon entry and expanded once inside a body cavity, thereby providing an increased spatial resolution. In this embodiment, the outside tube or member 26 is constructed of an expandable material, and the central tube or member 27 is constructed of a shape memory metal or polymer. Upon heating of the member 27 the member expands from the size shown in FIG. 6A to the size shown in FIG. 6B. Light pipes, not shown, can be located intermediate tubes or members 26 and 27, as in the FIG. 5 embodiment. As seen, when the member 26 is expanded as shown in FIG. 6B, such provides an increase in spatial resolution. Cooling of tube or member 26 allows the endoscope to contract and return to its smaller diameter as shown in FIG. 6A.

It has thus been shown that the present invention provides an improved endoscope which enable expanded utility of such an instrument by the incorporation therein of a multi-pupil imaging system and an access channel for other tools, etc. The endoscope of this invention provides an improved tool for use, for example, in laproscopic and videoscopic medical procedures, as well as enabling an extended use in non-medical applications imposing difficult to see or difficult access conditions.

While a particular embodiment of the invention has been illustrated and described, along with exemplary parameters, materials, etc., such are not intended to be limiting. Modifications and changes may become apparent to those skilled in the art, and it is intended that the invention be limited only by the scope of the appended claims.

The invention claimed is:

1. In an endoscope having means including fiber optics for illumination, the improvement comprising:
   a central access channel, and
   a multi-pupil imaging system positioned around said central access channel and (forming an annulus) around said central access channel.

2. The improvement of claim 1, wherein said multi-pupil imaging system is connected via a combining optics to a point of use selected from the group consisting of an image plane and stereographic or interferometric array.

3. The improvement of claim 2, wherein said multi-pupil imaging system is operatively connected to said combining optics via optics or fibers.

4. The improvement of claim 3, wherein said multi-pupil imaging system is located intermediate said fiber optics and said central access channel.

5. The improvement of claim 1, wherein said fiber optic are located centrally with respect to said multi-pupil imaging system.

6. The improvement of claim 1, wherein said multi-pupil imaging system includes a plurality of spaced lenses, and said fiber optics being interspersed among said lenses.

7. In an endoscope having fiber optics for illumination, the improvement comprising:
   a multi-pupil imaging system,
   said multi-pupil imaging system being located intermediate a pair of expandable/contractible members, whereby the spatial resolution can be changed by expansion or contraction of said members.

8. The improvement of claim 4, wherein said multi-pupil imaging system comprises a plurality of lenses.

9. An endoscope comprising:

three concentric members;

a first and second of said three concentric members forming a first annulus therebetween;

means for illumination being located in said first annulus;

a third and said second of said three concentric members forming a second annulus therebetween;

an imaging system being located in said second annulus; and a central access channel forming within said third of said three concentric members.

10. The endoscope of claim 9, wherein said means for illumination includes a plurality of fiber optic light pipes.

11. The endoscope of claim 9, wherein said imaging system comprises a multi-pupil imaging system.

12. The endoscope of claim 11, wherein said multi-pupil imaging system includes a plurality of lens located in said second annulus and around said central access channel.

13. The endoscope of claim 9, additionally including means operatively connecting said imaging system to an image plane or for stereographic or interferometric processing for depth and perspective information/visualization.

14. The endoscope of claim 9, wherein said means for illumination comprises a plurality of fiber optic light pipes adapted to be connected to a light source, and wherein said imaging system comprises a multi-pupil imaging system adapted to be connected to one of an image plane or stereographic or interferometric array processing.

15. The endoscope of claim 14, additionally including relay means for connected intermediate said multi-pupil imaging systems and a combining optics.

16. The endoscope of claim 14, wherein said multi-pupil imaging system comprises a plurality of lens.

17. An improved endoscope, comprising:

means forming an access channel;

means forming an annulus around said access channel;

means forming an imaging system located in said annulus; and means forming an illumination system.

18. The endoscope of claim 17, wherein said means forming an illumination system is positioned in said annulus.

19. The endoscope of claim 17, wherein said means forming an access channel and said means forming said annulus is each constructed of expandable/contractable material.

20. The endoscope of claim 17, additionally including means for forming an annulus around said imaging system, and wherein said means forming an illumination system is located in said last formed annulus.

21. The endoscope of claim 17, wherein said means forming an imaging system comprises a means forming a multi-pupil imaging system.

22. The endoscope of claim 17, wherein said means forming an illumination system includes a plurality of fiber optic light pipes adapted to be connected to a light source.

23. The endoscope of claim 22, wherein said means forming an imaging system includes a plurality of lens located around said access channel.

24. The endoscope of claim 17, additionally including means for forming an annulus within said access channel, and wherein said means forming an illumination system is located in said annulus formed within said access channel.

25. The endoscope of claim 17, wherein said means forming said access channel is constructed of a shape memory material, and wherein said means forming said annulus around said access channel is constructed of expandable/contractable material, whereby said access channel and said annulus can be increased in diameter to enable an increase in spatial resolution by said imaging system.

* * * * *